(12) United States Patent
Lewis et al.

(10) Patent No.: US 8,221,793 B2
(45) Date of Patent: *Jul. 17, 2012

(54) CHEMOEMBOLISATION

(75) Inventors: Andrew Lennard Lewis, Farnham (GB); Peter William Stratford, Farnham (GB); Simon Leppard, Farnham (GB); Pedro Garcia, Farnham (GB); Brenda Hall, Farnham (GB); Maria Victoria Fajardo Gonzalez, Farnham (GB)

(73) Assignee: Biocompatibles UK Limited, Surrey (GB)

( * ) Notice: Subject to any disclaimer, the term of this patent is extended or adjusted under 35 U.S.C. 154(b) by 905 days.

This patent is subject to a terminal disclaimer.

(21) Appl. No.: 12/210,573

(22) Filed: Sep. 15, 2008

(65) Prior Publication Data

US 2009/0022804 A1 Jan. 22, 2009

Related U.S. Application Data

(63) Continuation of application No. 11/434,274, filed on May 16, 2006, now Pat. No. 7,442,385, which is a continuation of application No. 10/366,603, filed on Feb. 14, 2003, now abandoned.

(30) Foreign Application Priority Data

Feb. 12, 2003 (EP) .................................... 03250868

(51) Int. Cl.
*A61K 9/14* (2006.01)
*A61K 9/16* (2006.01)

(52) U.S. Cl. ........................ 424/489; 424/497

(58) Field of Classification Search .................. 424/426, 424/422, 489, 497
See application file for complete search history.

(56) References Cited

U.S. PATENT DOCUMENTS

| 4,978,713 A | 12/1990 | Goldenberg |
| 5,508,317 A | 4/1996 | Muller |
| 5,583,163 A | 12/1996 | Muller |
| 5,782,974 A | 7/1998 | Sorensen et al. |
| 7,442,385 B2 * | 10/2008 | Lewis et al. ............ 424/426 |

FOREIGN PATENT DOCUMENTS

| EP | 0240424 B1 | 5/1991 |
| JP | 06-329542 A | 11/1994 |
| WO | 95/13798 | 5/1995 |
| WO | 97/45131 | 12/1997 |
| WO | 99/12577 A1 | 3/1999 |
| WO | 01/68720 A1 | 9/2001 |
| WO | WO 01/68720 * | 9/2001 |

OTHER PUBLICATIONS

Ball et al., "In Vitro Stability of Tris-acryl Gelatin Microspheres in a Multipharmaceutical Chemoembolization Solution," J. Vasc. Interv. Radiol., vol. 14, No. 1, (2003), pp. 83-88.
Juni et al., "Preparation and Evaluation in Vitro and in Vivo of Polyactic Acid Microspheres Containing Doxorubicin, "Chem. Parm. Bull., vol. 33, No. 1, (1985), pp. 313-318.
Jones et al., "Enhanced in vivo activity of adriamycin incorporated into controlled release microspheres," Br. J. Cancer, vol. 59, (1989), pp. 743-745.
Wingard et al., "Cell Surface Effects of Adriamycin and Carminomycin Immobilized on Cross-Linked Polyvinyl Alcohol," Cancer Research, vol. 45, Aug. 1985, pp. 3529-3536.
Benoit et al., "Microcapsules and Microspheres for Embolization and Chemoembolization," Polymeric Nanoparticles and Microspheres, and Guiot, et al., CRC Press, Boca Raton, FL, 1986, pp. 137,174.
Longo et al., "Preparation and Drug Release Properties of Albumin-Polyglutamic Acid-Adriamycin Microspheres," Polymer Preprints, 1985, vol. 24, pp. 56-57.
Sawaya et al., "Binding Mechanism of Doxorubicin in Ion-Exchange Albumin Microcapsules," J. Pharm. Sic., 1987, vol. 76, No. 6, pp. 475-480.
Codde, et al., "Reduced Toxicity of Adriamycin by Incorporation into Ion Exchange Microspheres: A Therapeutic Study Using a Rat Liver Tumour Model," Anticancer Research, 1990, vol. 10, No. 6, pp. 1715-1718.
Vora et al., "Investigation of the Relative Affinity of Doxorubicin for Neutral and Negatively Charged Particulate Carriers," Drug Development and Industrial Pharmacy, vol. 19, No. 7, 1993, pp. 759-771.

* cited by examiner

*Primary Examiner* — Blessing Fubara
(74) *Attorney, Agent, or Firm* — Sughrue Mion, PLLC

(57) ABSTRACT

A composition for chemoembolotherapy of solid tumors comprises particles of a water-insoluble water-swellable synthetic anionic polymer and, absorbed therein an anthracycline. Suitably the polymer is a poly(vinyl alcohol) based polymer and the drug is doxorubicin.

25 Claims, 3 Drawing Sheets

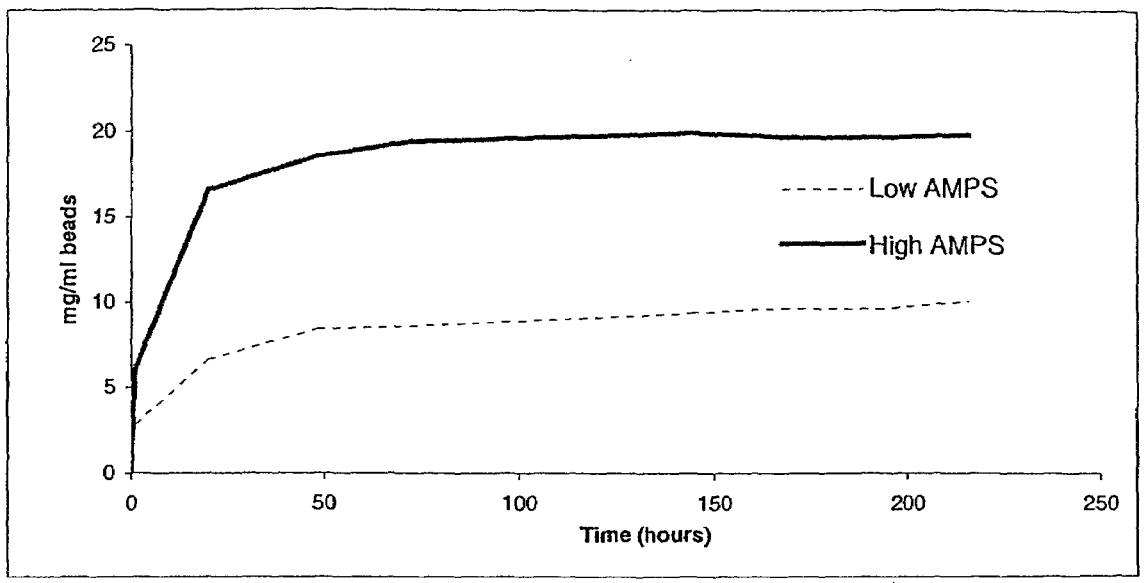
Figure 1: Loading of Low and High AMPS Formulations of Microspheres with Doxorubicin
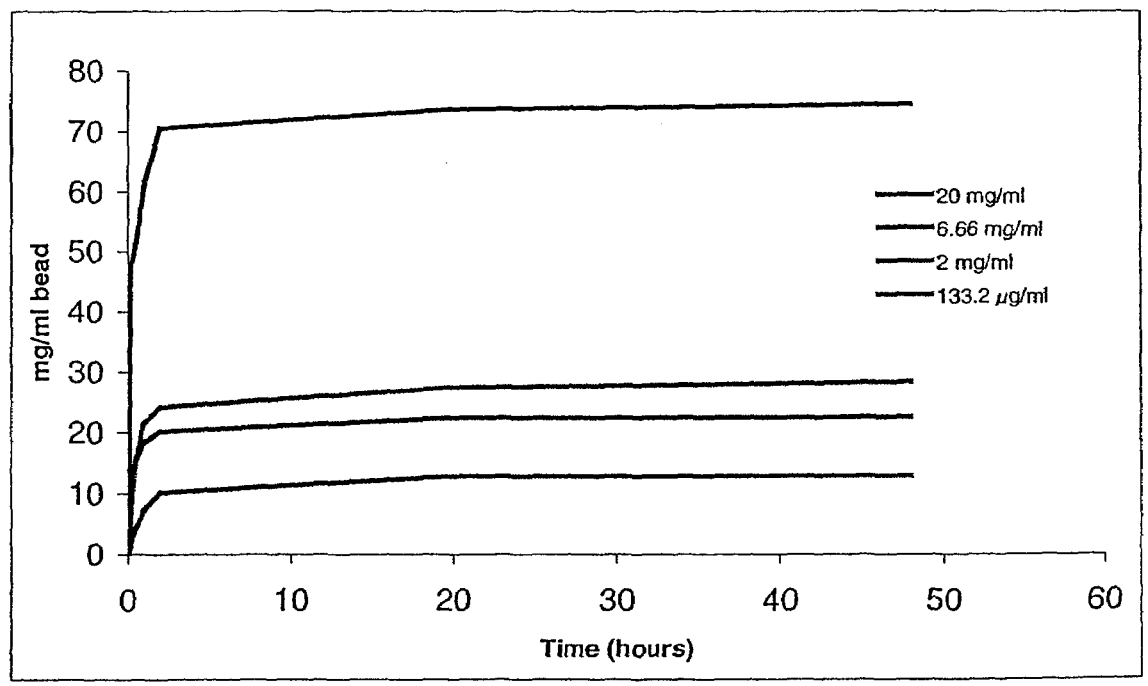
Figure 2: Effect of Doxorubicin concentration on Loading Profile for high AMPS Microspheres

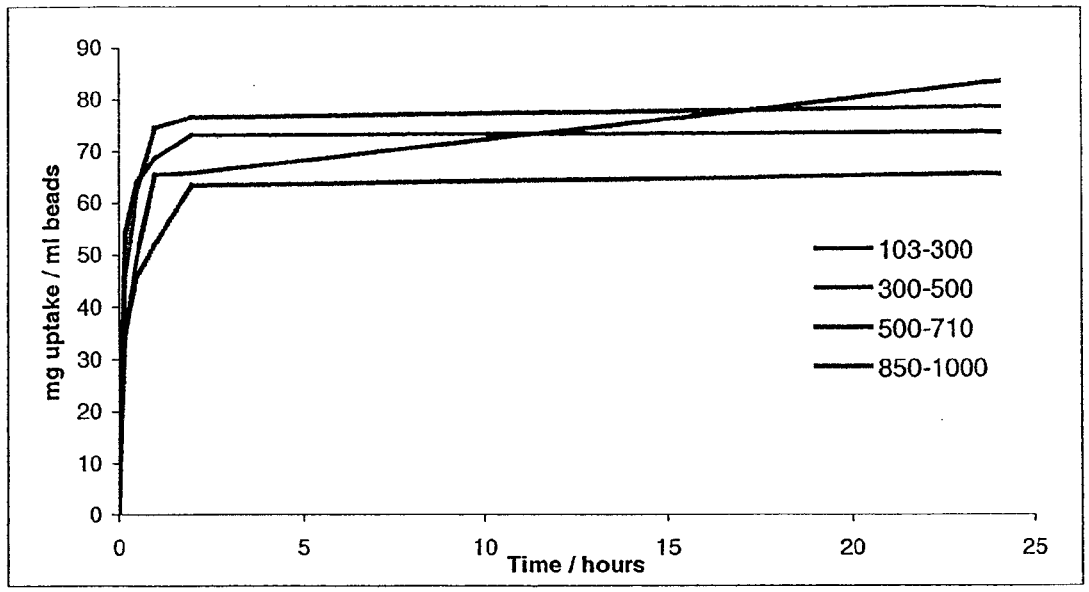
Figure 3: Effect of Microsphere Size Ranges on Doxorubicin Loading Profile
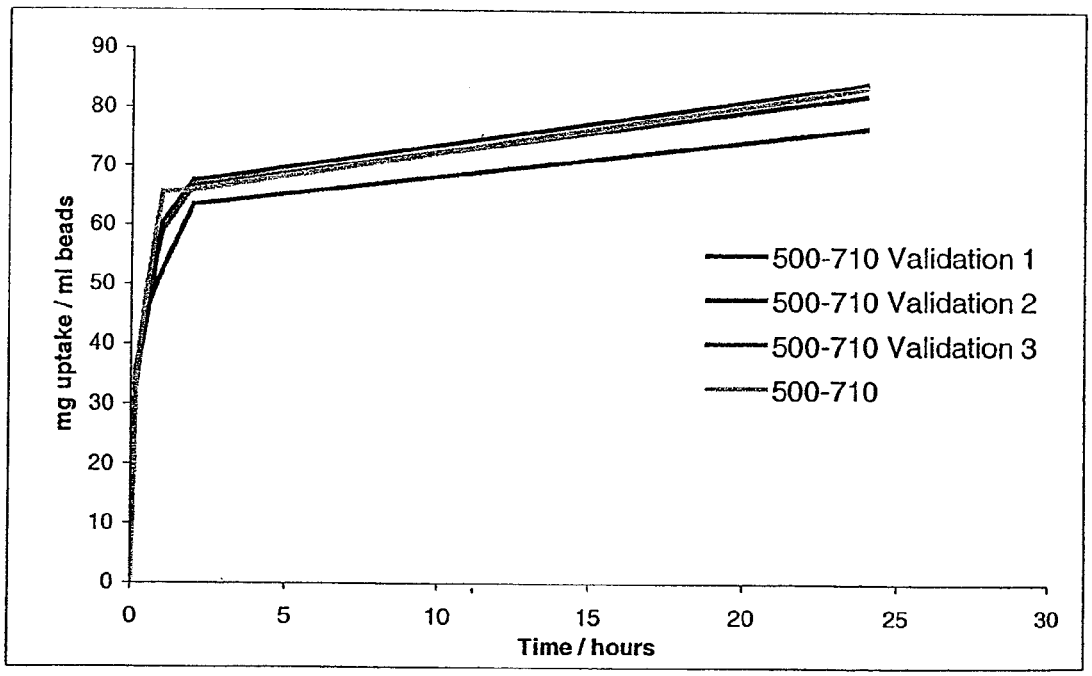
Figure 4: Reproducibility of Doxorubicin Loading into High AMPS Microspheres

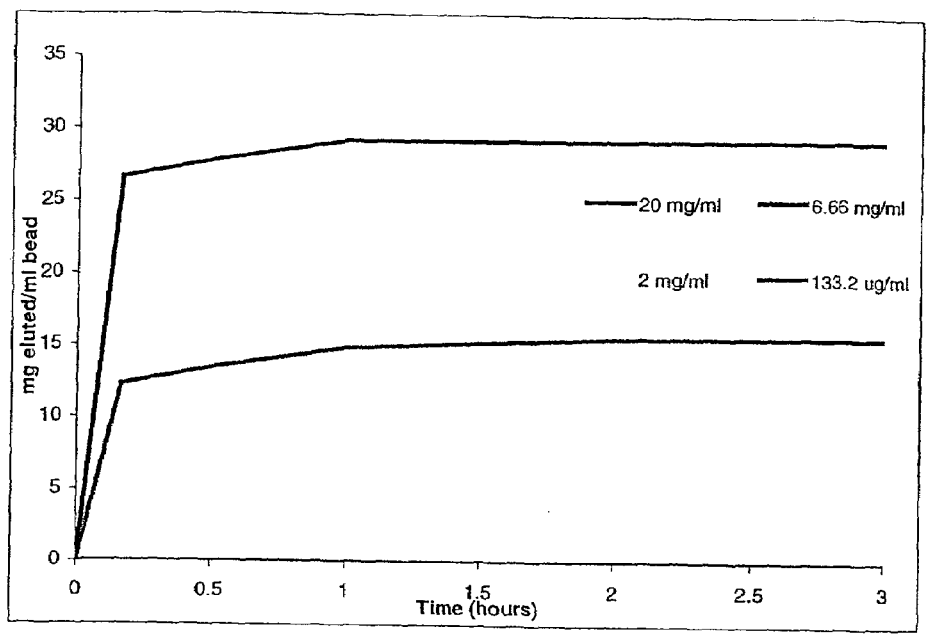
Figure 5: In-vitro Elution of Doxorubicin from High AMPS Microspheres
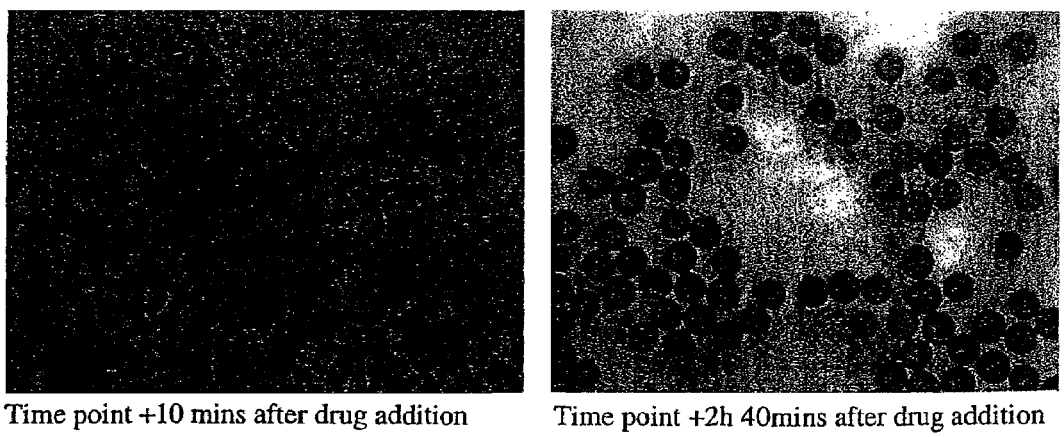
Time point +10 mins after drug addition    Time point +2h 40mins after drug addition
Figure 6: Doxorubicin Sequestration by High AMPS Bead Block

CHEMOEMBOLISATION

This is a continuation of application Ser. No. 11/434,274 filed May 16, 2006, which is a continuation of application Ser. No. 10/366,603 filed Feb. 14, 2003, which claims priority from European Patent Application No. 03250868.1, that was present on the filing date of the application. The entire disclosure of the prior application, application Ser. Nos. 11/434,274 and 10/366,603 is hereby incorporated by reference.

The present invention relates to compositions a polymeric embolic material and a therapeutic agent incorporated into the polymer matrix. The composition is of use for embolising tumours and delivering cytotoxic agents thereto.

Embolotherapy is a growing area of interventional medicine but normally relies upon the transarterial approach of the catheter to a desired location whereupon an agent is released in order to occlude a particular vessel. This treatment has been used in order to block the blood supply to certain hypervascularised tumours such as hepatocellular carcinoma and more recently is becoming a popular choice of treatment for uterine fibroids.

There is a range of embolic materials in clinical use, that require transcatheter delivery to the site of embolisation, whereupon they are released into the blood stream to block it. This is achieved either by a physical blocking of the vessel using small particles or spheres, or in the case of liquid embolic agents, require some sort of phase change or reaction to set the flowable material and form a cast within the vessel.

The most popular particulate-based embolic agent is poly(vinyl alcohol) (PVA) foam particles (e.g. Ivalon) which has been used for several decades. Recently, this material has been available in particulate, rather than sheet form, and does not require granulation by the surgeon prior to delivery.

In WO-A-0168720, PVA based compositions for embolotherapy are described. The PVA is, initially, derivatised to form a macromonomer, having pendant acrylic groups. Subsequently, these acrylic groups are polymerised, optionally in the presence of comonomer, to form a water-insoluble water-swellable polymer matrix. The polymerisation reaction may be carried out in situ, whereby the PVA is rendered water-insoluble after delivery into the vessel, at the embolisation site. Alternatively, the polymerisation is conducted prior to delivery, generally to form microspheres, which are delivered in suspension in an aqueous vehicle.

In WO-A-0168720, it is suggested that biologically active agents may be included in the embolic compositions, whereby active agent may be delivered from the formed hydrogel. One class of active agents is chemo therapeutic agents. Examples of chemo therapeutic agents are cisplatin, doxorubicin and mitomycin. Some general guidance is given as to methods of incorporating the active agents into the embolic compositions. Where the composition is a liquid which is cured in situ, the active may be simply mixed with the liquid. Where the articles are preformed, it is suggested that the active may be incorporated by "encapsulation", or by coating onto the surface. There are no worked examples in which a therapeutic agent is incorporated into any type of composition.

Microspheres of hydrogel material formed from poly(hydroxyethyl methacrylate), hydrolysed poly(methyl methacrylate) and PVA crosslinked using aldehyde crosslinking agents such as glutaraldehyde, have also been used as embolic agents. Hydroxyethyl methacrylate may be copolymerised with comonomers, for instance having acidic groups. For instance, a crosslinked copolymer of hydroxyethyl methacrylate with about 1-2 mole % acrylic acid cross-linked by 0.3-1.0 mole % ethylene glycol dimethacrylate, has an equilibrium water content in the range 55-60% by weight, and has been used as a contact lens formulation for many years.

One embolic product on the market is marketed by Biosphere, which comprises microspheres of trisacrylgelatin having a coating of collagen. Collagen has an overall cationic charge as physiological pH's. In Ball, D. S. et al., J. Vasc. Interv. Radiol. (2003), 14, 83-88, Biosphere show that the microspheres' mechanical characteristics are not adversely affected when admixed with a range of drugs commonly administered along with the embolic compositions. Doxorubicin, cisplatin and mitoxantrone are specifically tested.

Doxorubicin and other anthracyclines have been incorporated into a variety of polymeric matrices based delivery systems, such as microspheres of polylactides or polyglycolides and cross-linked fibrinogen and albumin microspheres. Juni, K. et al in Chem. Pharm. Bull. (1985), 33(1), 313-318 describe the incorporation of doxorubicin into poly(lactic acid) microspheres and the delivery of the composition intra arterially to dog liver. The composition embolised peripheral hepatic arteries. These types of microspheres are hard and are not easy to store and deliver. Doxorubicin has been covalently linked to the surface of cross-linked poly(vinyl alcohol) and tested for its cytotoxic properties (Wingard, L B et al. Cancer Research (1985) 45(8) 3529-3536). Since the drug is covalently bonded to the polymer it must be cleaved before being released from the surface and hence may not be released under physiological conditions.

Jones, C. et al in Brit. J. Cancer (1989) 59(5) describe incorporation of doxorubicin into ion-exchange microspheres and the use of the compositions in the chemoembolotherapy of tumours in a rat model.

A new composition according to the invention suitable for embolisation, comprises particles having a matrix of water-swellable water-insoluble polymer and, absorbed in the matrix, a water-soluble therapeutic agent, and is characterised in that the polymer has an overall anionic charge at a pH in the range 6 to 8, in that the particles, when swollen to equilibrium in water have particle sizes in the range 40-1500 µm and in that the therapeutic agent is an anthracycline compound having at least one amine group.

The polymer in the invention must be water-swellable, but water-insoluble. In the presence of aqueous liquid, therefore, the polymer will form a hydrogel. Generally the polymer is covalently crosslinked, although it may be appropriate for the polymer to be ionically crosslinked, at least in part. The polymer may be formed by polymerising ethylenically unsaturated monomers in the presence of di- or higher-functional crosslinking monomers, the ethylenically unsaturated monomers including an anionic monomer. Copolymers of hydroxyethyl methacrylate, acrylic acid and cross-linking monomer, such as ethylene glycol dimethacrylate or methylene bisacrylamide, as used for etafilcon A based contact lenses may be used.

Another type of polymer which may be used to form the water-swellable water-insoluble matrix is polyvinyl alcohol crosslinked using aldehyde type crosslinking agents such as glutaraldehyde. For such products, the polyvinyl alcohol must be rendered anionic, for instance by providing pendant anionic groups by reacting a functional acidic group containing monomer with the hydroxyl groups. Examples of suitable reagents are di-acids, for instance dicarboxylic acids.

The invention is of particular value where the polymer matrix is formed of a polyvinyl alcohol macromer, having more than one ethylenically unsaturated pendant group per molecule, by copolymerisation with ethylenically unsaturated monomers including an acidic monomer. The PVA macromer may be formed, for instance, by providing PVA polymer, of a suitable molecular weight such as in the range 1000 to 500,000 D, preferably 10,000 to 100,000 D, with pendant vinylic or acrylic groups. Pendant acrylic groups may be provided, for instance, by reacting acrylic or methacrylic acid with PVA to form ester linkages through some of the hydroxyl groups. Methods for attaching vinylic groups capable of polymerisation onto polyvinyl alcohol are described in, for instance, U.S. Pat. No. 4,978,713 and, preferably, U.S. Pat. Nos. 5,508,317 and 5,583,163. Thus the preferred macromer comprises a backbone of polyvinyl alcohol to which is linked, via a cyclic acetal linkage, to an (alk)acrylaminoalkyl moiety. Example 1 describes the synthesis of such a macromer. Preferably the PVA macromers have about 2 to 20 pendant ethylenic groups per molecule, for instance 5 to 10.

Where PVA macromers are copolymerised with ethylenically unsaturated monomers including an acidic monomer, the acidic monomer preferably has the general formula I $Y^1BQ$ in which $Y^1$ is selected from

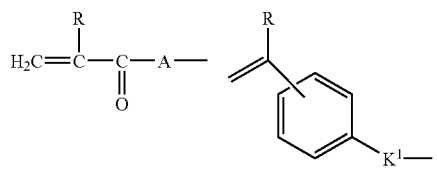

$CH_2=C(R)—CH_2—O—$, $CH_2=C(R)—CH_2OC(O)—$, $CH_2=C(R)OC(O)—$, $CH_2=C(R)—O—$, $CH_2=C(R)CH_2OC(O)N(R^1)—$, $R^2OOCCR=CRC(O)—O—$, $RCH=CHC(O)O—$, $RCH=C(COOR^2)CH_2—C(O)—O—$,

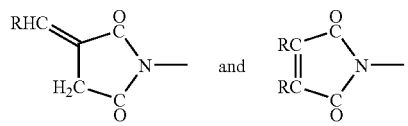

wherein:

R is hydrogen or a $C_1$-$C_4$ alkyl group;
$R^1$ is hydrogen or a $C_1$-$C_4$ alkyl group;
$R^2$ is hydrogen or a $C_{1-4}$ alkyl group or BQ where B and Q are as defined below;
A is —O— or —$NR^1$—;
$K^1$ is a group —$(CH_2)_rOC(O)$—, —$(CH_2)_rC(O)O$—, —$(CH_2)_rOC(O)O$—, —$(CH_2)_rNR^3$—, —$(CH_2)_rNR^3C(O)$—, —$(CH_2)_rC(O)NR^3$—, —$(CH_2)_rNR^3C(O)O$—, —$(CH_2)_rOC(O)NR^3$—, —$(CH_2)_rNR^3C(O)NR^3$— (in which the groups $R^3$ are the same or different), —$(CH_2)_rO$—, —$(CH_2)_rSO_3$—, or, optionally in combination with $B^1$, a valence bond and r is from 1 to 12 and $R^3$ is hydrogen or a $C_1$-$C_4$ alkyl group;
B is a straight or branched alkanediyl, oxyalkylene, alkanediyloxaalkanediyl, or alkanediyloligo(oxaalkanediyl) chain optionally containing one or more fluorine atoms up to and including perfluorinated chains or, if Q or $Y^1$ contains a terminal carbon atom bonded to B a valence bond; and
Q is an anionic group.

The anionic group may be, for instance, a carboxylate, carbonate, sulphonate, sulphate, nitrate, phosphonate or phosphate group, preferably a sulphonate group. The monomer may be polymerised as the free acid or in salt form. Preferably the $pK_a$ of the conjugate acid is less than 5.

In the monomer of general formula I preferably $Y^1$ is a group $CH_2=CRCOA-$ in which R is H or methyl, preferably methyl, and in which A is preferably NH. B is preferably an alkanediyl group of 1 to 12, preferably 2 to 6 carbon atoms.

One particularly preferred type of monomer is an (alk) acrylamido alkane-sulphonic acid, such as 2-acrylamido-2-methyl-1-propane-sulphonic acid (AMPS).

There may be included in the ethylenically unsaturated monomer diluent monomer, for instance non-ionic monomer. Such monomer may be useful to control the $pK_a$ of the acid groups, to control the hydrophilicity or hydrophobicity of the product, to provide hydrophobic regions in the polymer, or merely to act as inert diluent. Examples of non-ionic diluent monomer are, for instance, alkyl (alk)acrylates and (alk)acrylamides, especially such compounds having alkyl groups with 1 to 12 carbon atoms, hydroxy, and di-hydroxy-substituted alkyl(alk)acrylates and -(alk)acrylamides, vinyl lactams, styrene and other aromatic monomers.

The ethylenically unsaturated monomer may also include zwitterionic monomer, for instance to increase the hydrophilicity, lubricity, biocompatibility and/or hemocompatibility of the particles. Suitable zwitterionic monomers are described in our earlier publications WO-A-9207885, WO-A-9416748, WO-A-9416749 and WO-A-9520407. Preferably a zwitterionic monomer is 2-methacryloyloxy-2'-trimethylammonium ethyl phosphate inner salt (MPC).

In the polymer matrix, the level of anion is preferably in the range 0.1 to 10 meq $g^{-1}$, preferably at least 1.0 meq $g^{-1}$.

Where PVA macromer is copolymerised with other ethylenically unsaturated monomers, the weight ratio of PVA macromer to other monomer is preferably in the range of 50:1 to 1:5, more preferably in the range 20:1 to 1:2. In the ethylenically unsaturated monomer the anionic monomer is preferably present in an amount in the range 10 to 100 mole %, preferably at least 25 mole %.

Preferably the water-insoluble water-swellable polymer has an equilibrium water content measured by gravimetric analysis of 40 to 99 weight %, preferably 75 to 95%.

The polymer may be formed into particles in several ways. For instance, the crosslinked polymer may be made as a bulk material, for instance in the form of a sheet or a block, and subsequently be comminuted to the desired size. Alternatively, the crosslinked polymer may be formed as such in particulate form, for instance by polymerising in droplets of monomer in a dispersed phase in a continuous immiscible carrier. Examples of suitable water-in-oil polymerisations to produce particles having the desired size, when swollen, are known. For instance U.S. Pat. No. 4,224,427 describes processes for forming uniform spherical beads of up to 5 mm in diameter, by dispersing water-soluble monomers into a continuous solvent phase, in a presence of suspending agents. Stabilisers and surfactants may be present to provide control over the size of the dispersed phase particles. After polymerisation, the crosslinked microspheres are recovered by known means, and washed and optionally sterilised. Preferably the particles eg microspheres, are swollen in an aqueous liquid, and classified according to their size.

The therapeutic active used in the present invention is an anthracycline compound, which comprises an anthraquinone group to which is attached an amine sugar. The amino group on the sugar is believed to associate with the anionic groups in the polymer matrix, to allow high levels of loading and controlled delivery after administration.

Examples of suitable anthracyclines have the general formula II

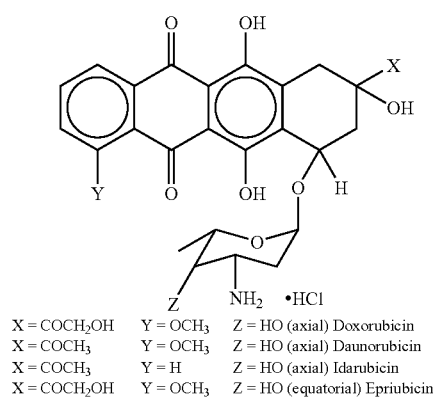

| | | |
|---|---|---|
| X = COCH$_2$OH | Y = OCH$_3$ | Z = HO (axial) Doxorubicin |
| X = COCH$_3$ | Y = OCH$_3$ | Z = HO (axial) Daunorubicin |
| X = COCH$_3$ | Y = H | Z = HO (axial) Idarubicin |
| X = COCH$_2$OH | Y = OCH$_3$ | Z = HO (equatorial) Epriubicin |

We have found that doxorubicin, which has been thoroughly tested for efficacy on various tumours, has particularly interesting loading and release characteristics. The drug appears to have a particular affinity for poly(vinyl alcohol-graft-acrylamido propane sulphonic acid), so that high levels of doxorubicin are capable of incorporation into the polymer, and release over many days.

In the invention it is important that the drug is not covalently attached to the polymer matrix.

The therapeutic active may be incorporated into the polymer matrix by a variety of techniques. In one method, the therapeutic active may be mixed with a precursor of the polymer, for instance a monomer or macromer mixture or a cross-linkable polymer and cross-linker mixture, prior to polymerising or crosslinking. Alternatively, the active may be loaded into the polymer after it has been crosslinked. For instance, particulate dried polymer may be swollen in a solution of therapeutic active, preferably in water, optionally with subsequent removal of non-absorbed agent and/or evaporation of solvent. A solution of the active, in an organic solvent such as an alcohol, or, more preferably, in water, may be sprayed onto a moving bed of particles, whereby drug is absorbed into the body of the particles with simultaneous solvent removal. Most conveniently, we have found that it is possible merely to contact swollen particles suspended in a continuous liquid vehicle, such as water, with a solution of drug, over an extended period, whereby drug becomes absorbed into the body of the particles. This is believed to be analogous to a cation exchange type process. The swelling vehicle may subsequently be removed or, conveniently, may be retained with the particles as part of the product for subsequent use as an embolic agent.

Alternatively, the suspension of particles can be filtered to remove any remaining drug loading solution and the particles dried by any of the classical techniques employed to dry pharmaceutical-based products. This could include, but is not limited to, air drying at room or elevated temperatures or under reduced pressure or vacuum; classical freeze-drying; atmospheric pressure-freeze drying; solution enhanced dispersion of supercritical fluids (SEDS). Alternatively the drug-loaded microspheres may be dehydrated using an organic solvent to replace water in a series of steps, followed by evaporation of the more volatile organic solvent. A solvent should be selected which is a non solvent for the drug.

In brief, a typical classical freeze drying process might proceed as follows: the sample is aliquoted into partially stoppered glass vials, which are placed on a cooled, temperature controlled shelf within the freeze dryer. The shelf temperature is reduced and the sample is frozen to a uniform, defined temperature. After complete freezing, the pressure in the dryer is lowered to a defined pressure to initiate primary drying. During the primary drying, water vapour is progressively removed from the frozen mass by sublimation whilst the shelf temperature is controlled at a constant, low temperature. Secondary drying is initiated by increasing the shelf temperature and reducing the chamber pressure further so that water absorbed to the semi-dried mass can be removed until the residual water content decreases to the desired level. The vials can be sealed, in situ, under a protective atmosphere if required.

Atmospheric pressure freeze drying is accomplished by rapidly circulating very dry air over a frozen product. In comparison with the classical freeze-drying process, freeze-drying without a vacuum has a number of advantages. The circulating dry gas provides improved heat and mass transfer from the frozen sample, in the same way as washing dries quicker on a windy day. Most work in this area is concerned with food production, and it has been observed that there is an increased retention of volatile aromatic compounds, the potential benefits of this to the drying of biologicals is yet to be determined. Of particular interest is the fact that by using atmospheric spray drying processes instead of a cake, a fine, free-flowing powder is obtained. Particles can be obtained which have submicron diameters, this is tenfold smaller than can be generally obtained by milling. The particulate nature, with its high surface area results in an easily rehydratable product, currently the fine control over particle size required for inhalable and transdermal applications is not possible, however there is potential in this area.

The composition which is administered to a patient in need of embolotherapy having a solid tumour, for instance a hepatocellular carcinoma, is an aqueous suspension of swollen particles containing absorbed drug. It is often desirable for the suspension to be mixed prior to delivery with an imaging agent such as a conventional radiopaque agent, as is used for gel type embolic compositions. Alternatively or additionally the particles may be pre-loaded with radiopaque material, in addition to the anthracycline. The composition which is administered may also be admixed with other therapeutic agents, or may be administered in separately but in combination with other therapeutic agents. Usually the composition is administered from a reservoir in a syringe using the conventional delivery devices, such as an intra-arterial catheter.

There is provided as a second aspect of the invention the use of an anthracycline compound in the manufacture of a composition for use in the treatment of a solid tumour by embolotherapy, in which treatment the anthracycline is delivered from a polymer matrix formed by the copolymerisation of a poly(vinyl alcohol) macromer having at least 2 pendant ethylenically unsaturated groups per molecule and an ethylenically unsaturated anionic monomer.

In this aspect of the invention the polymer matrix may be formed in situ. Thus a liquid composition comprising the macromer and the anionic monomer and anthracycline may be delivered into the circulation of a patient and subjected to conditions to initiate polymerisation at the target site whereby an embolising gel is formed. Alternatively the polymer matrix may be preformed before administration, as described in the first aspect of the invention.

The PVA macromer and anionic monomer are preferably as described above in connection with the first aspect. Other monomers may also be copolymerised, as described in connection with the first aspect of the invention.

The present invention is illustrated in the following examples for which the results are shown in the figures as follows.

FIG. 1 shows the results of example 2;
FIG. 2 shows the results of example 3;
FIG. 3 shows the results of example 4;
FIG. 4 shows the results of example 5;
FIG. 5 shows the results of example 6; and
FIG. 6 shows the results of example 7.

EXAMPLE 1

Outline Method for the Preparation of Microspheres

Nelfilcon B Macromer Synthesis:

The first stage of microsphere synthesis involves the preparation of Nelfilcon B—a polymerisable macromer from the widely used water soluble polymer PVA. Mowiol 8-88 poly (vinyl alcohol) (PVA) powder (88% hydrolised, 12% acetate content, average molecular weight about 67,000 D) (150 g) (Clariant, Charlotte, N.C. USA) is added to a 2 liter glass reaction vessel. With gentle stirring, 1000 ml water is added and the stirring increased to 400 rpm. To ensure complete dissolution of the PVA, the temperature is raised to 99±9° C. for 2-3 hours. On cooling to room temperature N-acryloylaminoacetaldehyde (NAAADA) (Ciba Vision, Germany) (2.49 g or 0.104 mmol/g of PVA) is mixed in to the PVA solution followed by the addition of concentrated hydrochloric acid (100 ml) which catalyses the addition of the NAAADA to the PVA by transesterification. The reaction proceeds at room temperature for 6-7 hours then stopped by neutralisation to pH 7.4 using 2.5M sodium hydroxide solution. The resulting sodium chloride plus any unreacted NAAADA is removed by diafiltration (step 2).

Diafiltration of Macromer:

Diafiltration (tangential flow filtration) works by continuously circulating a feed solution to be purified (in this case nelfilcon B solution) across the surface of a membrane allowing the permeation of unwanted material (NaCl, NAAADA) which goes to waste whilst having a pore size small enough to prevent the passage of the retentate which remains in circulation.

Nelfilcon B diafiltration is performed using a stainless steel Pellicon 2 Mini holder stacked with 0.1 $m^2$ cellulose membranes having a pore size with a molecular weight cut off of 3000 (Millipore Corporation, Bedford, Mass. USA). Mowiol 8-88 has a weight average molecular weight of 67000 and therefore has limited ability to permeate through the membranes.

The flask containing the macromer is furnished with a magnetic stirrer bar and placed on a stirrer plate. The solution is fed in to the diafiltration assembly via a Masterflex LS peristaltic pump fitted with an Easy Load II pump head and using LS24 class VI tubing. The Nelfilcon is circulated over the membranes at approximately 50 psi to accelerate permeation. When the solution has been concentrated to about 1000 ml the volume is kept constant by the addition of water at the same rate that the filtrate is being collected to waste until 6000 ml extra has been added. Once achieved, the solution is concentrated to 20-23% solids with a viscosity of 1700-3400 cP at 25° C. Nelfilcon is characterised by GFC, NMR and viscosity.

Microsphere Synthesis:

The spheres are synthesised by a method of suspension polymerisation in which an aqueous phase (nelfilcon B) is added to an organic phase (butyl acetate) where the phases are immiscible. By employing rapid mixing the aqueous phase can be dispersed to form droplets, the size and stability of which can be controlled by factors such as stirring rates, viscosity, ratio of aqueous/organic phase and the use of stabilisers and surfactants which influence the interfacial energy between the phases. Two series of microspheres are manufactured, a low AMPS and a higher AMPS series, the formulation of which are shown below.

A High AMPS:
Aqueous: ca 21% w/w Nelfilcon B solution (400±150 g approx)
  ca 50% w/w 2-acryamido-2-methylpropanesulphonate Na salt (140±10 g)
  Purified water (137±30 g)
  Potassium persulphate (5.22±0.1 g)
  Tetramethyl ethylene diamine TMEDA (6.4±0.1 ml)
Organic: n-Butyl acetate (2.7±0.3 L)
  10% w/w cellulose acetate butyrate in ethyl acetate (46±0.5 g) (stabiliser)
  Purified water (19.0±0.5 ml)

B Low AMPS:
Aqueous: ca 21% w/w Nelfilcon B solution (900±100 g approx)
  ca 50% w/w 2-acryamido-2-methylpropanesulphonate Na salt (30.6±6 g)
  Purified water (426±80 g)
  Potassium persulphate (20.88±0.2 g)
  TMEDA (25.6±0.5 ml)
Organic: n-Butyl acetate (2.2±0.3 L)
  10% w/w cellulose acetate butyrate (CAB) in ethyl acetate (92±1.0 g)
  Purified water (16.7±0.5 ml)

A jacketed 4000 ml reaction vessel is heated using a computer controlled bath (Julabo PN 9-300-650) with feedback sensors continually monitoring the reaction temperature.

The butyl acetate is added to the reactor at 25° C. followed by the CAB solution and water. The system is purged with nitrogen for 15 minutes before the PVA macromer is added. Cross linking of the dispersed PVA solution is initiated by the addition of TMEDA and raising the temperature to 55° C. for three hours under nitrogen. Crosslinking occurs via a redox initiated polymerisation whereby the amino groups of the TMEDA react with the peroxide group of the potassium persulphate to generate radical species. These radicals then initiate polymerisation and crosslinking of the double bonds on the PVA and AMPS transforming the dispersed PVA-AMPS droplets into insoluble polymer microspheres. After cooling to 25° C. the product is transferred to a filter reactor for purification where the butyl acetate is removed by filtration followed by:

Wash with 2×300 ml ethyl acetate to remove butyl acetate and CAB
Equilibrate in ethyl acetate for 30 mins then filtered
Wash with 2×300 ml ethyl acetate under vacuum filtration
Equilibrate in acetone for 30 mins and filter to remove ethyl acetate, CAB and water
Wash with 2×300 ml acetone under vacuum filtration
Equilibrate in acetone overnight
Wash with 2×300 ml acetone under vacuum
Vacuum dry, 2 hrs, 55° C. to remove residual solvents.

Dyeing:

This step is optional but generally unnecessary when drug is loaded with a coloured active (as this provides the colour). When hydrated the microsphere contains about 90% (w/w) water and can be difficult to visualise. To aid visualisation in a clinical setting the spheres are dyed blue using reactive blue #4 dye (RB4). RB4 is a water soluble chlorotriazine dye which under alkaline conditions will react with the pendant hydroxyl groups on the PVA backbone generating a covalent ether linkage. The reaction is carried out at pH12 (NaOH) whereby the generated HCl will be neutralised resulting in NaCl.

Prior to dyeing the spheres are fully re-hydrated and divided into 35 g aliquots (treated individually). Dye solution is prepared by dissolving 0.8 g RB4 in 2.5M NaOH solution (25 ml) and water (15 ml) then adding to the spheres in 2 l of 80 g/l$^{-1}$ saline. After mixing for 20 mins the product is collected on a 32 μm sieve and rinsed to remove the bulk of the unreacted dye.

Extraction:

An extensive extraction process is used to remove any unbound or non specifically adsorbed RB4. The protocol followed is as shown:

Equilibrate in 2 l water for 5 mins. Collect on sieve and rinse. Repeat 5 times

Equilibrate in 2 l solution of 80 mM disodium hydrogen phosphate in 0.29% (w/w) saline. Heat to boiling for 30 mins. Cool, collect on sieve and wash with 1 l saline. Repeat twice more.

Collect, wash on sieve the equilibrate in 2 l water for 10 mins.

Collect and dehydrate in 1 l acetone for 30 mins.

Combine all aliquots and equilibrate overnight in 2 l acetone.

Sieving:

The manufactured microsphere product ranges in size from 100 to 1200 microns and must undergo fractionation through a sieving process using a range of mesh sizes to obtain the nominal distributions listed below.

1. 100-300 μm
2. 300-500 μm
3. 500-700 μm
4. 700-900 μm
5. 900-1200 μm

Prior to sieving the spheres are vacuum dried to remove any solvent then equilibrated at 60° C. in water to fully re-hydrate. The spheres are sieved using a 316L stainless steel vortisieve unit (MM Industries, Salem Ohio) with 15" stainless steel sieving trays with mesh sizes ranging from 32 to 1000 μm. Filtered saline is recirculated through the unit to aid fractionation. Spheres collected in the 32 micron sieve are discarded.

EXAMPLE 2

Loading of Doxorubicin

For this experiment the low AMPS microspheres prepared as in example 1 were used. For each size of bead used, 0.5 ml was transferred in to 2, 1 ml syringes, one for drug take up and the second to act as a control. The sizes chosen for the experiment were, 106-300 μm, 300-500 μm, 500-710 μm and 850-1000 μm. Additionally a further 3 syringes of the 500-710 μm were prepared in order to validate the procedure. 11, 10 ml glass vials were covered in foil, to prevent degradation of the doxorubicin by light for the duration of the experiment. A standard curve was created. Using the 80 ml, 20 mg/ml drug solution, the following concentrations were prepared and their absorbances (at 483 nm) measured: 100 μg/ml, 50 μg/ml, 25 μg/ml, 12.5 μg/ml, 6.25 μg/ml and 3.125 μg/ml. The resulting absorbances were plotted on a graph and the equation of the line used to calculate the concentration of drug that was up-taken by the beads in the experiment. Four of the vials were filled with 5 ml of distilled water (ROMIL) to be used as controls when the beads were added. To the remaining 7 vials were added 5 ml of the drug solution at the desired concentration. The starting absorbance and therefore concentration of the solution was already known from the preparation of the standard curve. (In order to measure the absorbance of the 20 mg/ml solution it was necessary to dilute it 200 times, using the concentration 100 μg/ml. This 1:200 dilution was carried through for the duration of measuring the uptake of the solution by the beads.) The stopwatch was started as soon as the first set of microspheres were added to the first drug containing vial, microspheres were added to each of the remaining 6 vials working from smallest to largest. Once sealed using the caps they were placed on the rotary mixer. The process was repeated for the control samples. The absorbances were measured in the same order as the vials were set up at time intervals of 0.167 hr (10 min), 0.5 hr, 1 hr, 2 hr, 24 hr and 96 hr. From the data the amount of drug (in mg) per 1 ml of microspheres and the % uptake of drug by 1 ml of microspheres could be calculated. The results are shown in FIG. 1.

EXAMPLE 3

Effect of Drug Concentration on Loading

Following the procedure outline in Example 2, it was possible to load a range of different concentrations of Doxorubicin into the high AMPS microsphere formulation. The majority of the drug was seen to load into the microspheres (500-710 μm size range) within a few hours (see FIG. 2). The loading can be seen to be far higher than for the low AMPS formulation on a weight basis.

EXAMPLE 4

Effect of Microsphere Size on Loading

Loading of doxorubicin was conducted on several different size ranges of microspheres to enable comparison of the uptake. Whilst the smaller microspheres were seen to load drug more rapidly, continued loading over a 24 hour period suggests that an equivalent weight of microspheres will equilibrate to about the same drug loading. The more rapid uptake is attributed to increased surface area of the smaller microspheres (see FIG. 3).

EXAMPLE 5

Reproducibility of Loading

The loading experiments outlined in example 2 were repeated a number of times in order to measure the reproducibility in loading of the doxorubicin. High AMPS microspheres of 500-710 μm size range were loaded from a 20 mg/ml drug solution in water and the drug uptake monitored over time (FIG. 4).

EXAMPLE 6

Elution of Doxorubicin from Microspheres

High AMPS microspheres were loaded with various concentrations of doxorubicin and the microspheres eluted into 250 ml of distilled water (FIG. 5).

The drug eluting from the 133.2 μg/ml and 2 mg/ml loaded microspheres was still below the detection limit at 3 hours. For the higher drug loadings, a burst effect is evident in the first few minutes, followed by a prolonged period of slower release. It is surmised that the burst represents the free drug eluting from the water held within the microspheres, whereas the prolonged elution results from the drug that is "bound" into the spheres essentially by ionic interaction between the charged groups. For the highest loading of drug (from the 20 mg/ml loading solution), the burst effect represents some 45% of the total drug loading of the spheres, the remainder taking several days to completely elute from the carrier. Studies have shown that 100% of the drug is eventually eluted from the microspheres.

EXAMPLE 7

Visualisation of Doxorubicin Sequestration by High AMPS microspheres

To a vial containing ca 0.5 g of High AMPS microspheres in the size range 850-1000 μm (hand sieved), 1 ml of doxorubicin in phosphate buffered saline PBS (66.6 μg/ml) and 3 ml of PBS was added. The microspheres were placed under a CCD camera, and images taken every 2 mins for a period of 2.5 hrs. No agitation of the sample occurred in this time period, but small movements were observed due to localised thermal heating from the light source. The initial and final microspheres are thus identical, and can be compared over the time period. The uptake of drug was observed by the increase in red colour in the microspheres, and the depletion of the surrounding solution (FIG. 6):

EXAMPLE 8

Preparation of Dried Drug-Loaded Microspheres

Microspheres can be loaded with doxorubicin by the method outlined in example 2. The microspheres are dehydrated using the following procedure: The microspheres to be dehydrated were placed in a plastic container and covered with a 10% acetone (ROMIL) solution made in PBS (Inverclyde Biologicals). The microspheres were left in the solution for 10 minutes during which time they were agitated for 30 seconds several times. The solution was then decanted off and the process repeated twice more. This procedure was repeated with increasing acetone concentrations of 25%, 50%, 75% and finally 100%. After the final 100% dehydration step the acetone was decanted off and the beads placed in an oven set to 50° C. and dried to constant mass.

The resulting dried product can be resuspended/rehydrated in saline/contrast media prior to the embolisation procedure. Hydration is rapid taking only a few minutes to swell to >80% of the fully hydrated size.

The invention claimed is:

1. A composition comprising particles having a matrix of water-swellable water-insoluble polymer and, absorbed in the matrix, a water-soluble therapeutic agent, and is characterised in that the polymer has an overall anionic charge at a pH in the range 6 to 8, in that the particles, when swollen to equilibrium in water have particle sizes in the range 40-1500 μm and in that the therapeutic agent is an anthracycline compound having at least one amine group, wherein the level of anion in the polymer matrix is in the range of 0.1 to 10 meq/g, the polymer comprises poly(vinyl alcohol) and the particles are microspheres.

2. A composition according to claim 1 in which the polymer is covalently cross-linked.

3. A composition according to claim 1 in which the polymer comprises cross-linked poly(vinyl alcohol).

4. A composition according to claim 3 formed by copolymerising poly(vinyl alcohol) macromer having at least two pendant ethylenically unsaturated groups per molecule with ethylenically unsaturated monomers including anionic monomer.

5. A composition according to claim 4 in which the anionic monomer has the general formula I

in which $Y^1$ is selected from

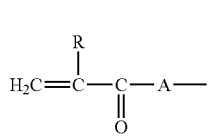 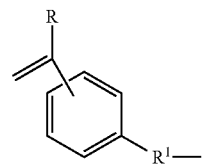

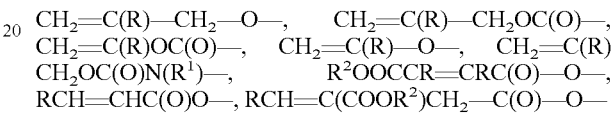

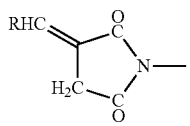 and 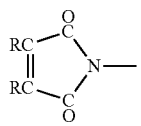

wherein

R is hydrogen or a $C_1$-$C_4$ alkyl group;

$R^1$ is hydrogen or a $C_1$-$C_4$ alkyl group;

$R^2$ is hydrogen or a $C_{1-4}$ alkyl group or BQ where B and Q are as defined below;

A is —O— or —$NR^1$—;

$K^1$ is a group —$(CH_2)_r$OC(O)—, —$(CH_2)_r$C(O)O—, —$(CH_2)_r$OC(O)O—, —$(CH_2)_r$$NR^3$—, —$(CH_2)_r$$NR^3$C(O)—, —$(CH_2)_r$C(O)$NR^3$—, —$(CH_2)_r$$NR^3$C(O)O—, —$(CH_2)_r$OC(O)$NR^3$—, —$(CH_2)_r$$NR^3$C(O)$NR^3$— (in which the groups $R^3$ are the same or different), —$(CH_2)_r$O—, —$(CH_2)_r$$SO_3$—, or, optionally in combination with $B^1$, a valence bond and r is from 1 to 12 and $R^3$ is hydrogen or a $C_1$-$C_4$ alkyl group;

B is a straight or branched alkanediyl, oxaalkylene, alkanediyloxaalkanediyl, or alkanediyloigo(oxaalkanediyl) chain optionally containing one or more fluorine atoms up to and including perfluorinated chains or, if Q or $Y^1$ contains a terminal carbon atom bonded to B a valence bond; and Q is an anionic group.

6. A composition according to claim 5 in which $Y^1$ is $CH_2$=CRCOA in which R is H or methyl, A is NH, and in which B is $C_{1-12}$ alkanediyl.

7. A composition according to claim 5 in which Q is a carboxylate, carbonate, sulphonate, sulphate, nitrate, phosphonate or phosphate group.

8. A composition according to claim 4 in which the poly(vinyl alcohol) macromer has average molecular weight in the range 1,000 to 500,000 D.

9. A composition according to claim 4 in which the pendant ethylenic groups are linked via cyclic acetal linkages with oxygen atoms from adjacent hydroxyl groups.

10. A composition according to claim 1 in which the anthracycline is a compound of the general formula II

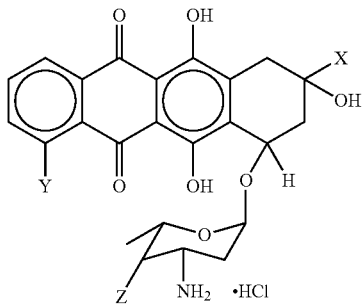

| | | |
|---|---|---|
| X = COCH₂OH | Y = OCH₃ | Z = HO (axial) Doxorubicin |
| X = COCH₃ | Y = OCH₃ | Z = HO (axial) Daunorubicin |
| X = COCH₃ | Y = H | Z = HO (axial) Idarubicin |
| X = COCH₂OH | Y = OCH₃ | Z = HO (equatorial) Epriubicin | preferably doxorubicin.

11. A composition according to claim 1 in which the particles are swollen with and suspended in an aqueous liquid.

12. A composition according to claim 11 further comprising an imaging agent.

13. A composition according to claim 12, wherein the imaging agent is a radiopaque agent.

14. A method of embolotherapy of a patient having a solid tumour, in which the composition of claim 1 is administered to form an embolus in the circulation.

15. Process for producing a composition according to claim 1 in which particles of a polymer are contacted with a solution of the anthracycline in the presence of water whereby anthracycline is absorbed into the matrix of the polymer.

16. Process according to claim 15 in which the contacting is carried out by suspending the polymer particles in an aqueous solution of the anthracycline.

17. Process according to claim 16 in which the particles of polymer with anthracycline absorbed in the matrix are recovered from the suspension and dried.

18. A composition according to claim 1, wherein the water-insoluble water-swellable polymer has an equilibrium water content measured by gravimetric analysis in the range of 40-99 wt %.

19. A composition according to claim 1, wherein the water-insoluble water-swellable polymer has an equilibrium water content measured by gravimetric analysis in the range of 75-95 wt %.

20. A composition according to claim 1, wherein the anthracycline is doxorubicin.

21. A composition according to claim 1, wherein the particles are swollen with and suspended in an aqueous liquid.

22. A composition according to claim 21, further comprising an imaging agent.

23. A method for treatment comprising administering the composition of claim 22, to a patient suffering from a solid tumor, whereby an embolus is formed containing the particles.

24. A composition according to claim 22, wherein the imaging agent is a radiopaque agent.

25. A method of embolotherapy of a patient having a solid tumour, in which an anthracycline compound having at least one amine group is delivered from a composition comprising particles having a matrix of water-swellable water-insoluble polymer and, absorbed in the matrix, the anthracycline compound, and is characterised in that the polymer has an overall anionic charge at a pH in the range 6 to 8, in that the particles, when swollen to equilibrium in water have particle sizes in the range 40-1500 μm, wherein the level of anion in the polymer matrix is in the range of 0.1 to 10 meq/g, the polymer comprises poly(vinyl alcohol) and the particles are microspheres, and wherein the polymer matrix is formed by the copolymerisation of a poly(vinyl alcohol) macromer having at least 2 pendant ethylenically unsaturated groups per molecule and an ethylenically unsaturated anionic monomer.

* * * * *

UNITED STATES PATENT AND TRADEMARK OFFICE
CERTIFICATE OF CORRECTION

PATENT NO.         : 8,221,793 B2
APPLICATION NO.    : 12/210573
DATED              : July 17, 2012
INVENTOR(S)        : Andrew Lennard Lewis et al.

Page 1 of 1

It is certified that error appears in the above-identified patent and that said Letters Patent is hereby corrected as shown below:

Column 1, Line 10: delete "compositions a polymeric" and insert --compositions comprising a polymeric--

Column 2, Line 13: delete "polymeric matrices based" and insert --polymeric matrix-based--

Column 4, Line 23: delete "hemocompatibility" and insert --haemocompatibility--

Column 7, Line 61: delete "GFC" and insert --GPC--

Column 9, Line 49: delete "low AMPS" and insert --low and high AMPS--

Column 10, Line 29: delete "basis." and insert --basis (Fig. 1).--

Column 12, Line 15: delete

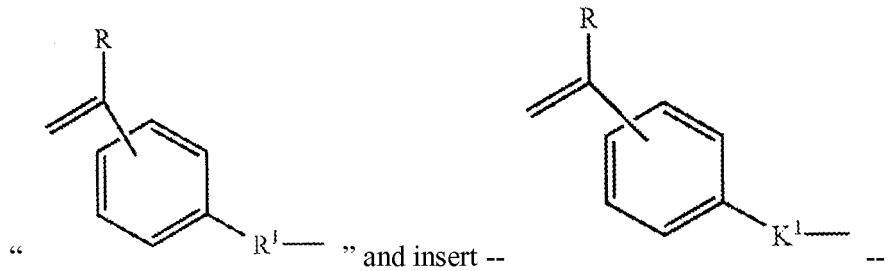

Signed and Sealed this
Twenty-sixth Day of February, 2013

Teresa Stanek Rea
*Acting Director of the United States Patent and Trademark Office*